United States Patent [19]
Hugentobler et al.

[11] Patent Number: 5,750,900
[45] Date of Patent: May 12, 1998

[54] ACOUSTIC STRAIN GAUGE AND ASSEMBLY AND METHOD FOR MEASURING STRAIN

[75] Inventors: Monte K. Hugentobler, Novato; Efrain Anthony Mandracchia, San Francisco, both of Calif.

[73] Assignee: SonicForce, L.L.C., Burlingame, Calif.

[21] Appl. No.: 792,695

[22] Filed: Jan. 29, 1997

Related U.S. Application Data

[63] Continuation-in-part of Ser. No. 707,922, Sep. 9, 1996.
[51] Int. Cl.⁶ .................................................. G01N 29/24
[52] U.S. Cl. ............................... 73/779; 73/643; 73/597
[58] Field of Search ............................. 73/643, 597, 779, 73/598, 599, 600; 324/209

[56] References Cited

U.S. PATENT DOCUMENTS

| | | |
|---|---|---|
| 3,850,028 | 11/1974 | Thompson et al. . |
| 3,877,294 | 4/1975 | Shaw . |
| 4,013,905 | 3/1977 | Breneman et al. . |
| 4,048,847 | 9/1977 | Alers et al. . |
| 4,080,836 | 3/1978 | Thompson et al. . |
| 4,092,868 | 6/1978 | Thompson et al. . |
| 4,104,922 | 8/1978 | Alers et al. . |
| 4,127,035 | 11/1978 | Vasile . |
| 4,184,374 | 1/1980 | Thompson et al. . |
| 4,218,924 | 8/1980 | Fortunko et al. . |
| 4,232,557 | 11/1980 | Vasile . |
| 4,246,793 | 1/1981 | Fairand et al. . |
| 4,248,092 | 2/1981 | Vasile et al. . |
| 4,344,663 | 8/1982 | Ognier et al. . |
| 4,593,567 | 6/1986 | Isselstein et al. . |
| 5,085,082 | 2/1992 | Cantor et al. . |
| 5,170,366 | 12/1992 | Passarelli . |

FOREIGN PATENT DOCUMENTS

| 0031639 | 3/1981 | Japan | 73/643 |

Primary Examiner—Hezron E. Williams
Assistant Examiner—Rose M. Miller
Attorney, Agent, or Firm—Coudert Brothers

[57] ABSTRACT

The present invention defines an improved strain gauge and a method of using an electromagnetic acoustic transducer (EMAT) for monitoring stress and strain in an underlying workpiece. The gauge is provided with positioning pins for fixing the registration of the EMAT relative to the workpiece. The gauge is provided with a friction reducing means, such as a bearing or a wheel assembly, to minimize EMAT bottom contact surface area and thus unwanted frictional influences caused by deformation of the workpiece under the EMAT. An assembly for reliably positioning the EMAT gauge above a workpiece is also disclosed, in which the assembly comprises an actuating means which by a linkage mechanism lowers or raises at least the EMAT into position, further allowing access to the positioning pins for applying the necessary force to fix the position of the gauge relative to the workpiece.

32 Claims, 11 Drawing Sheets

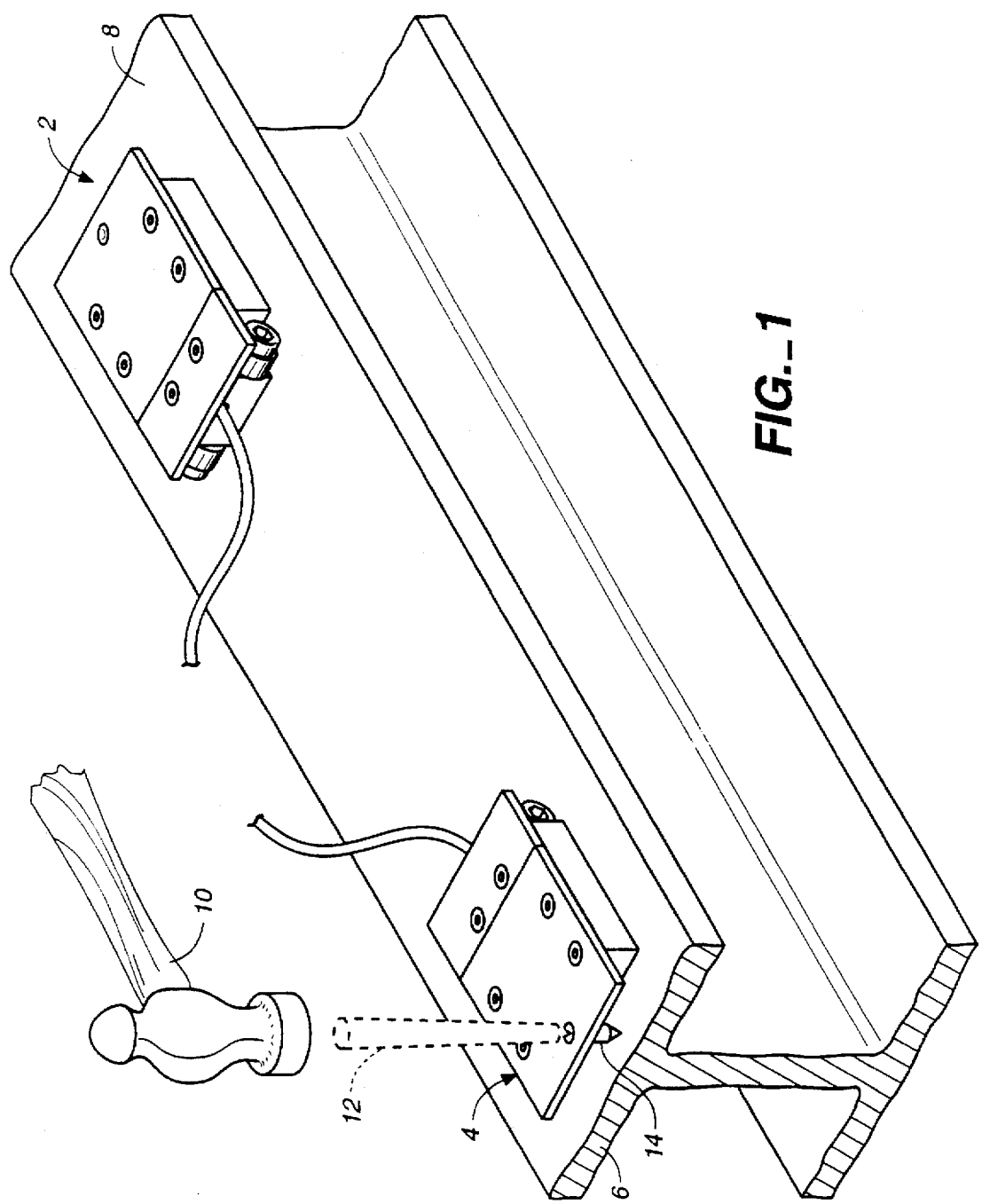
FIG._1

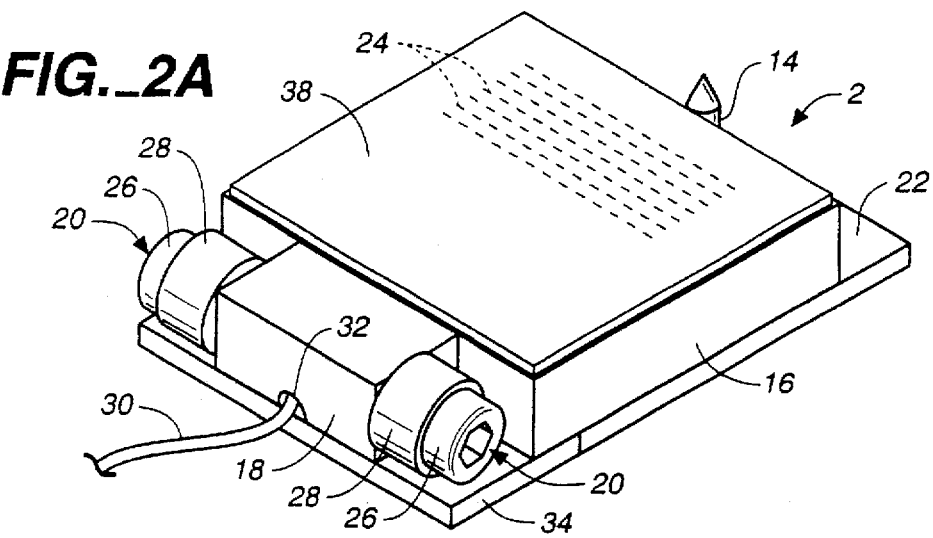
*FIG._2A*
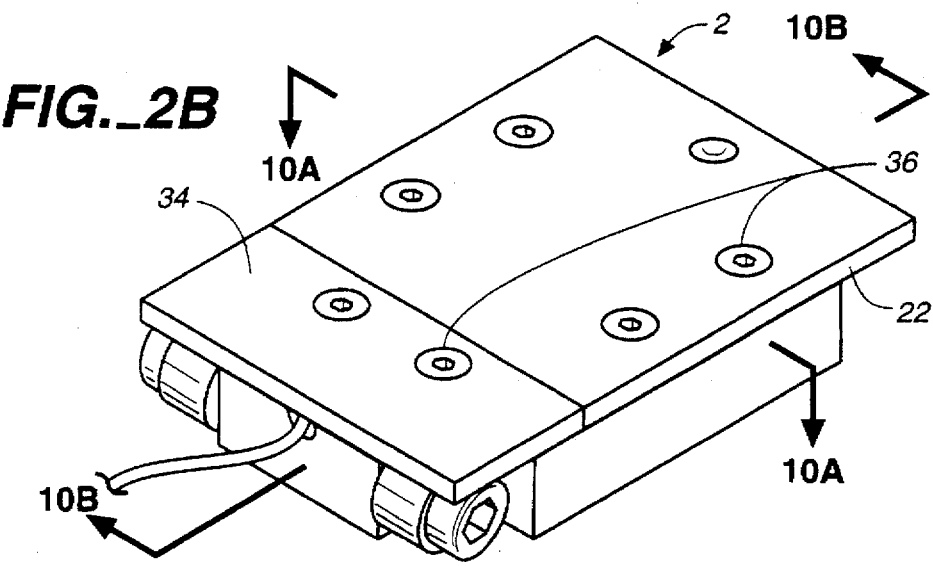
*FIG._2B*
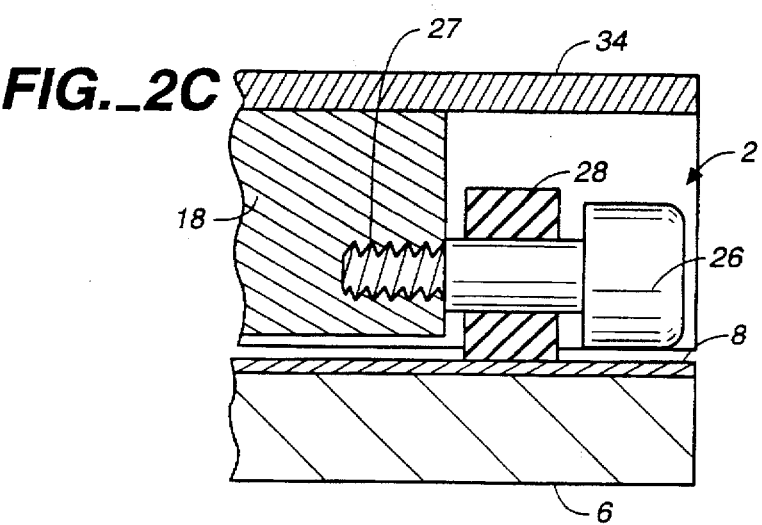
*FIG._2C*

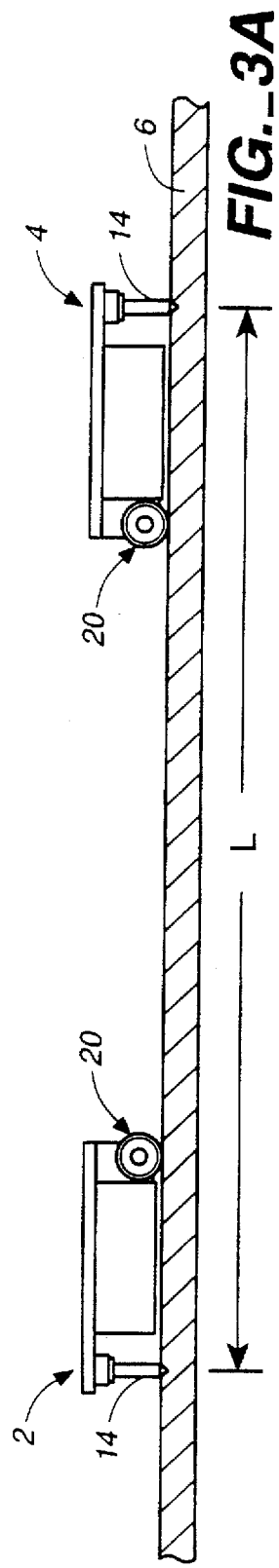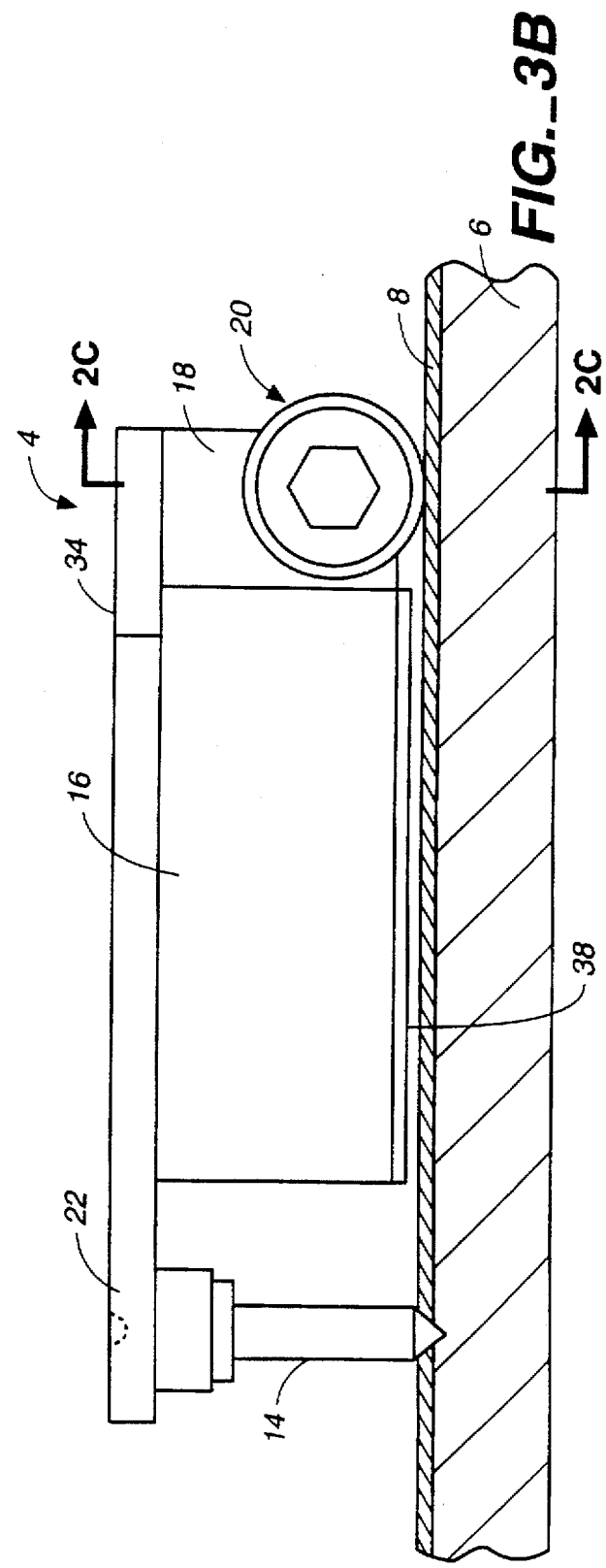

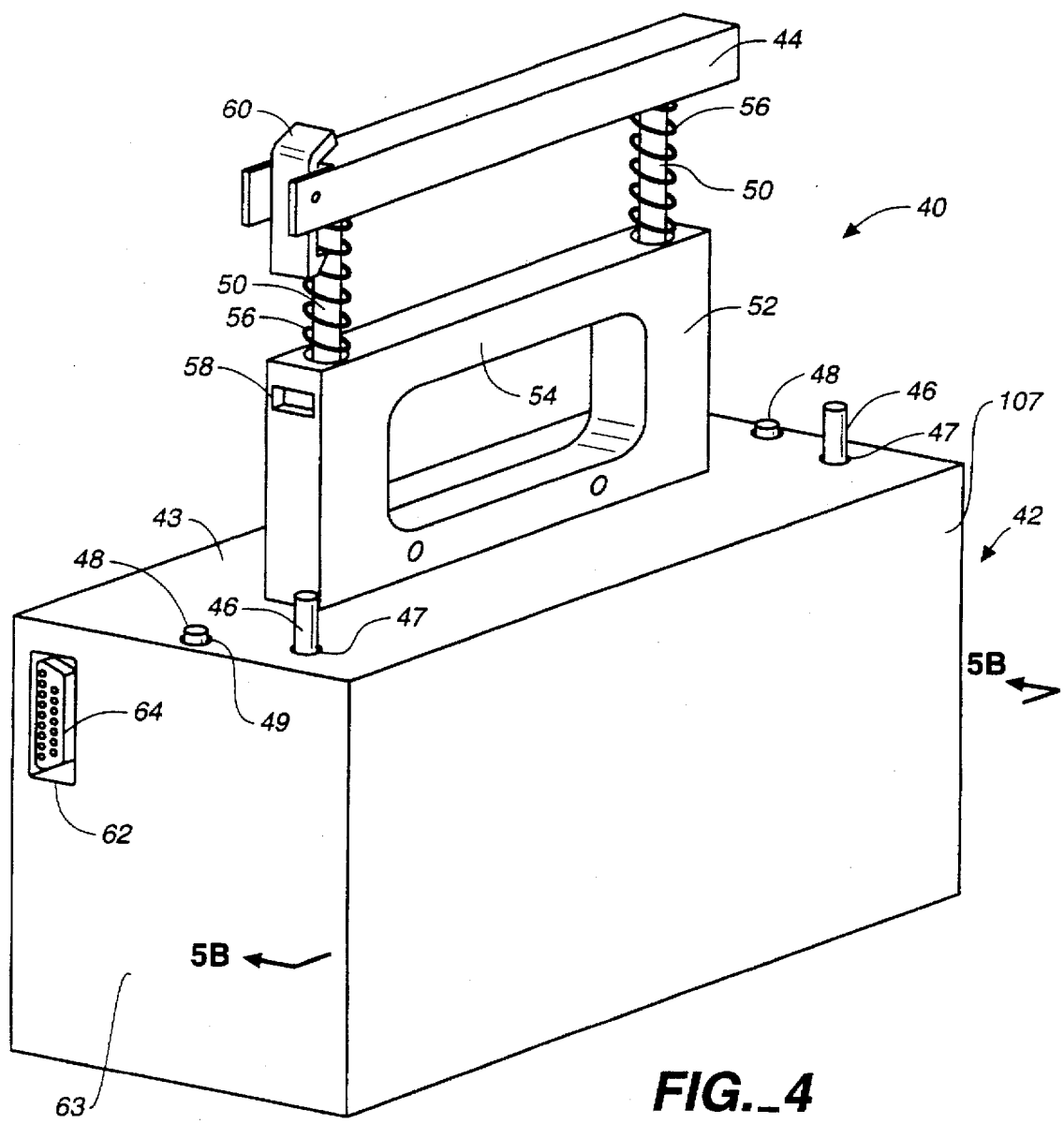
FIG._4

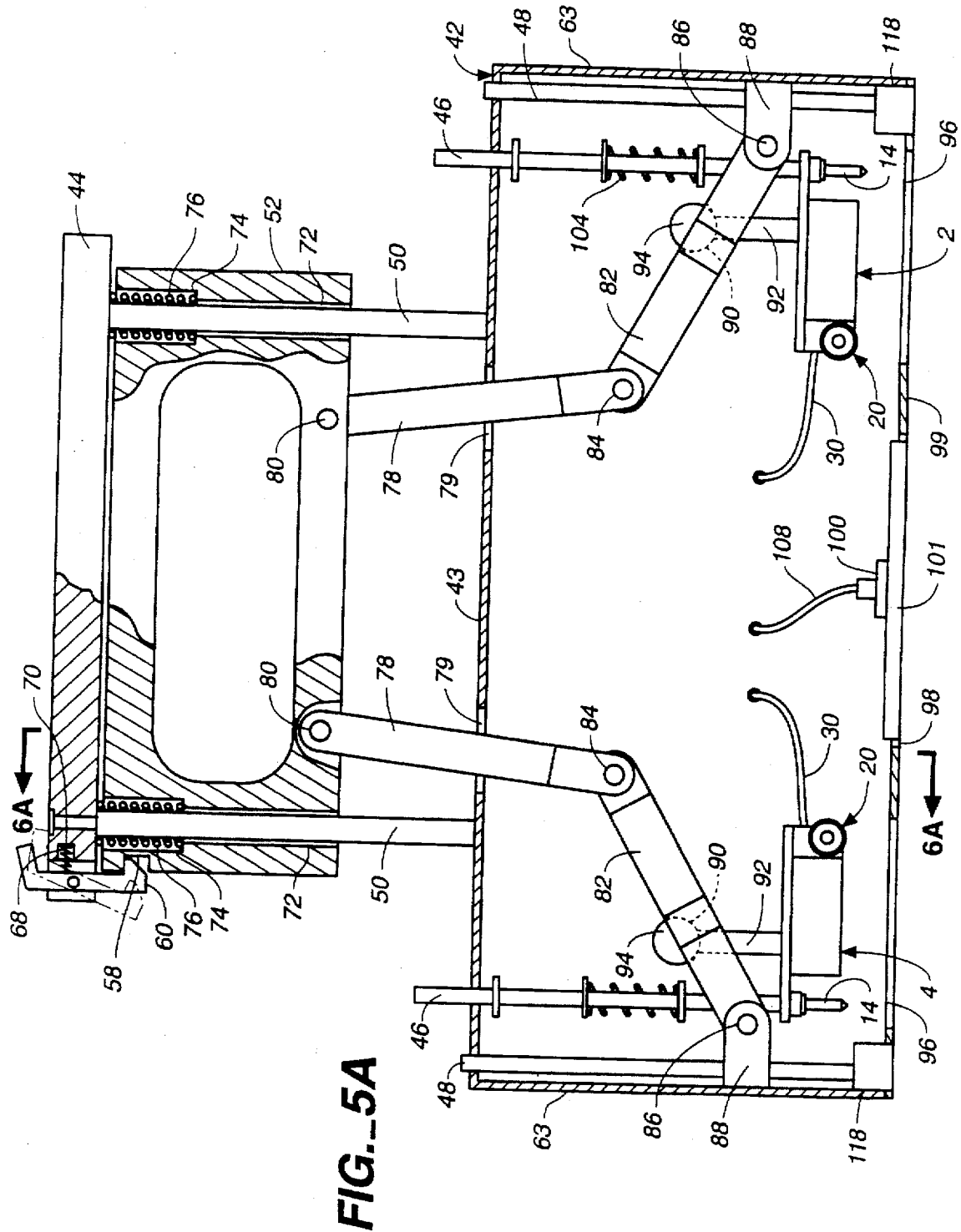
FIG._5A

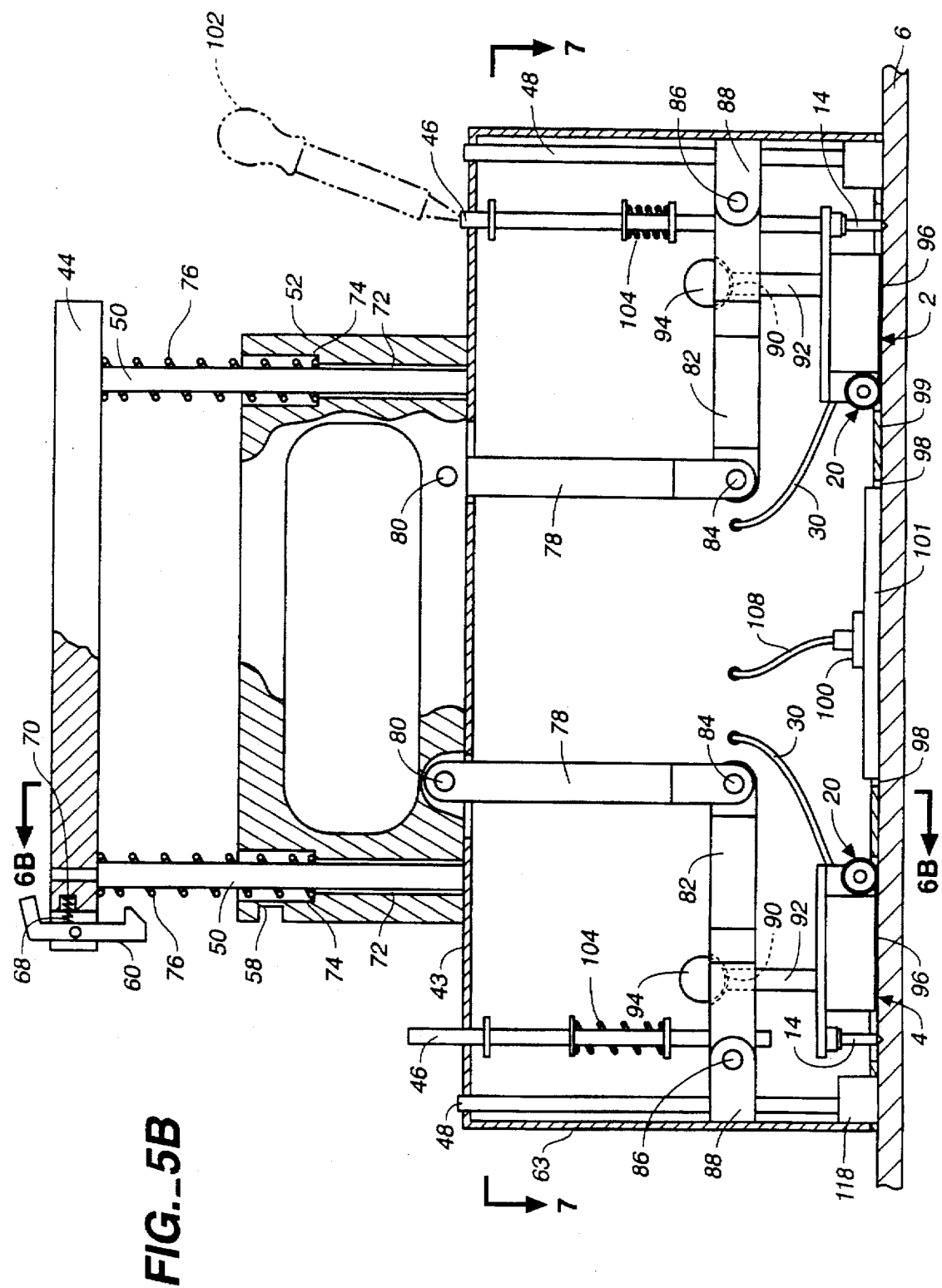
FIG._5B

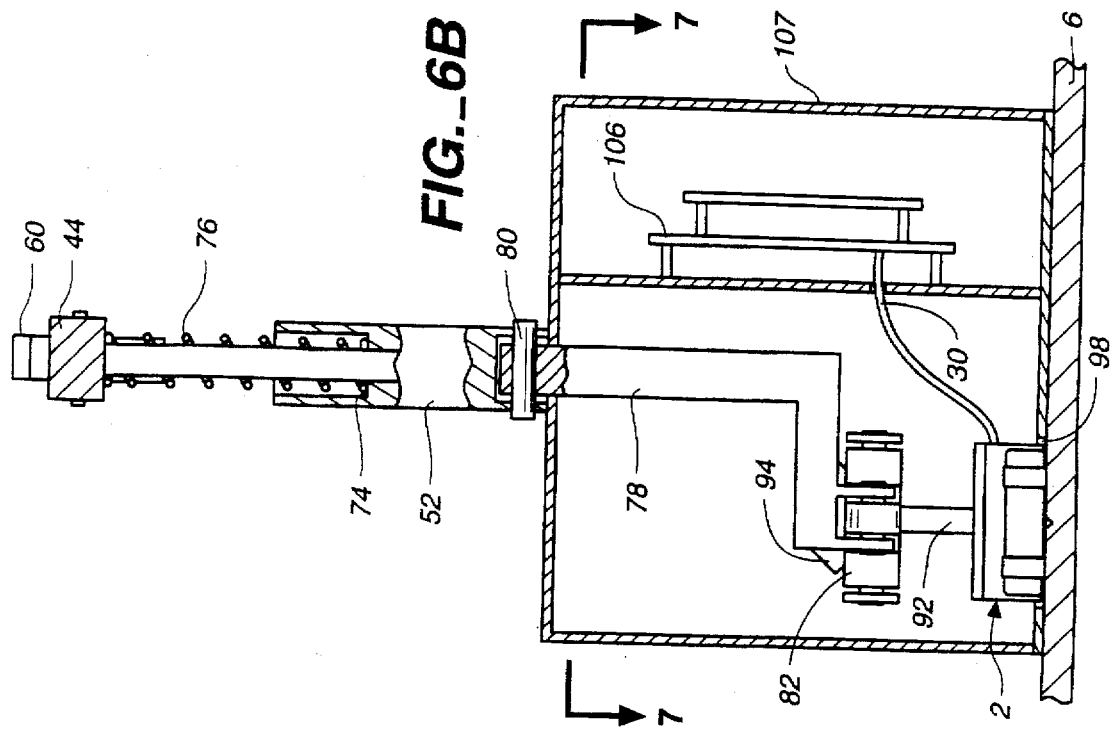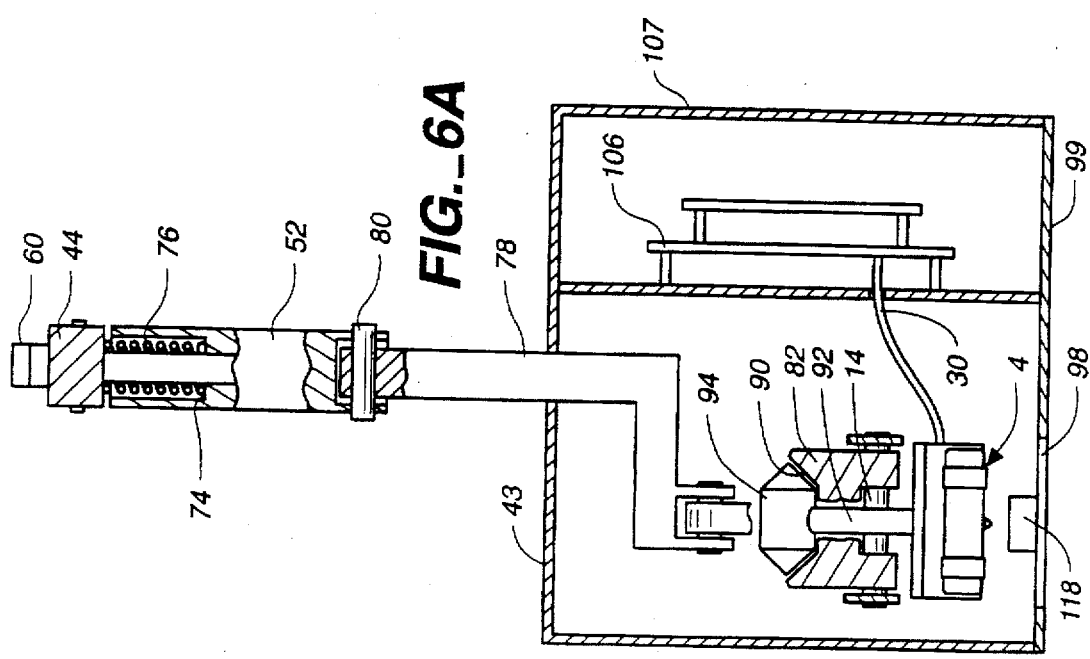

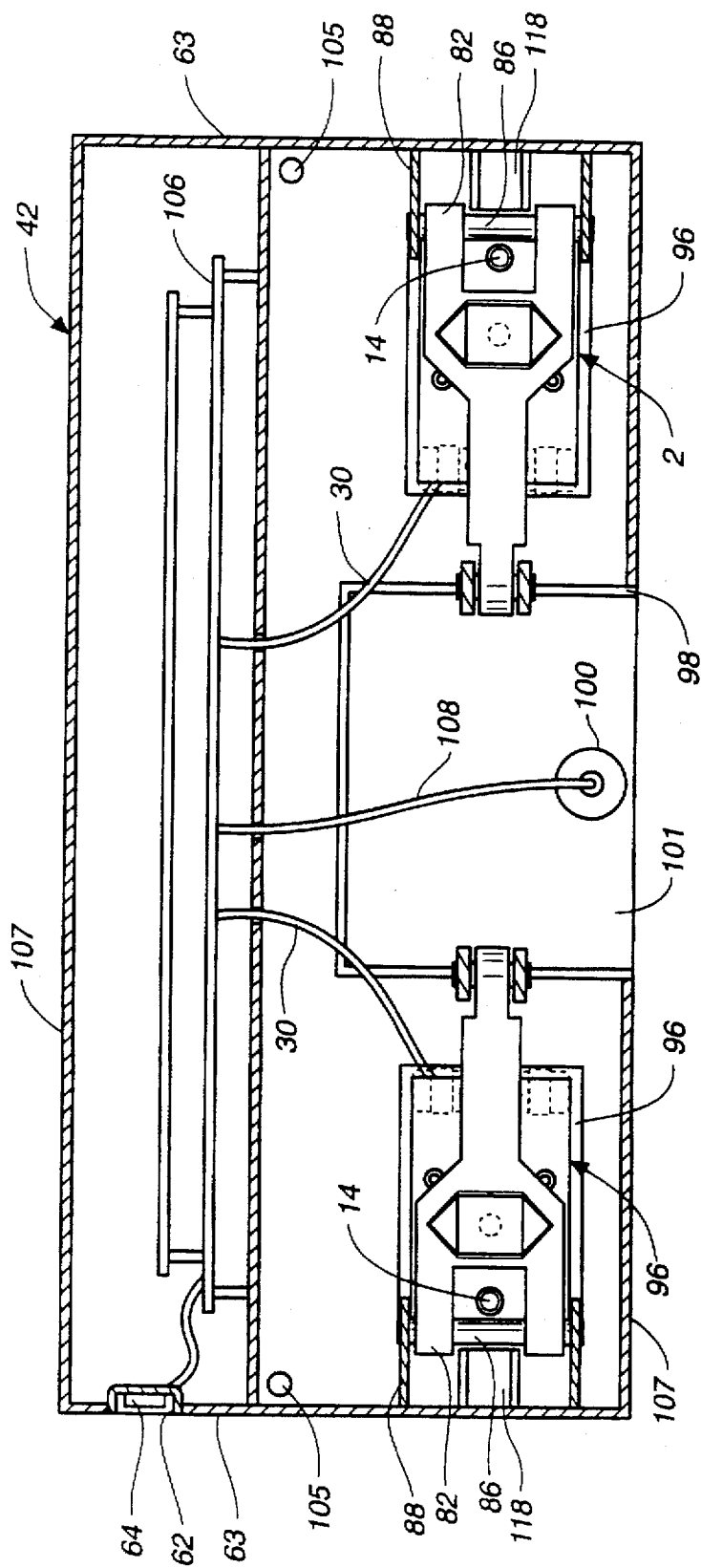
FIG._7

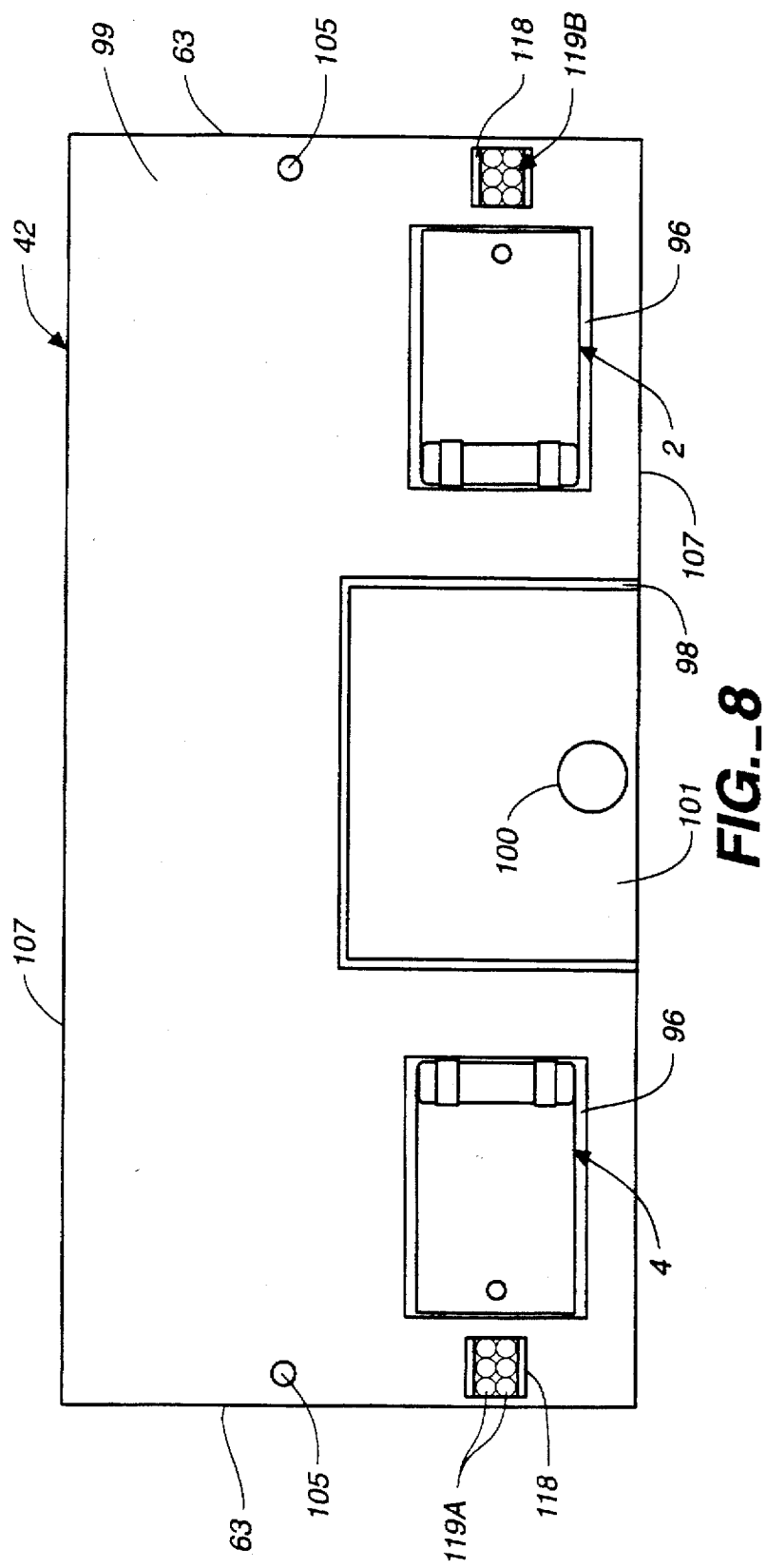
FIG._8

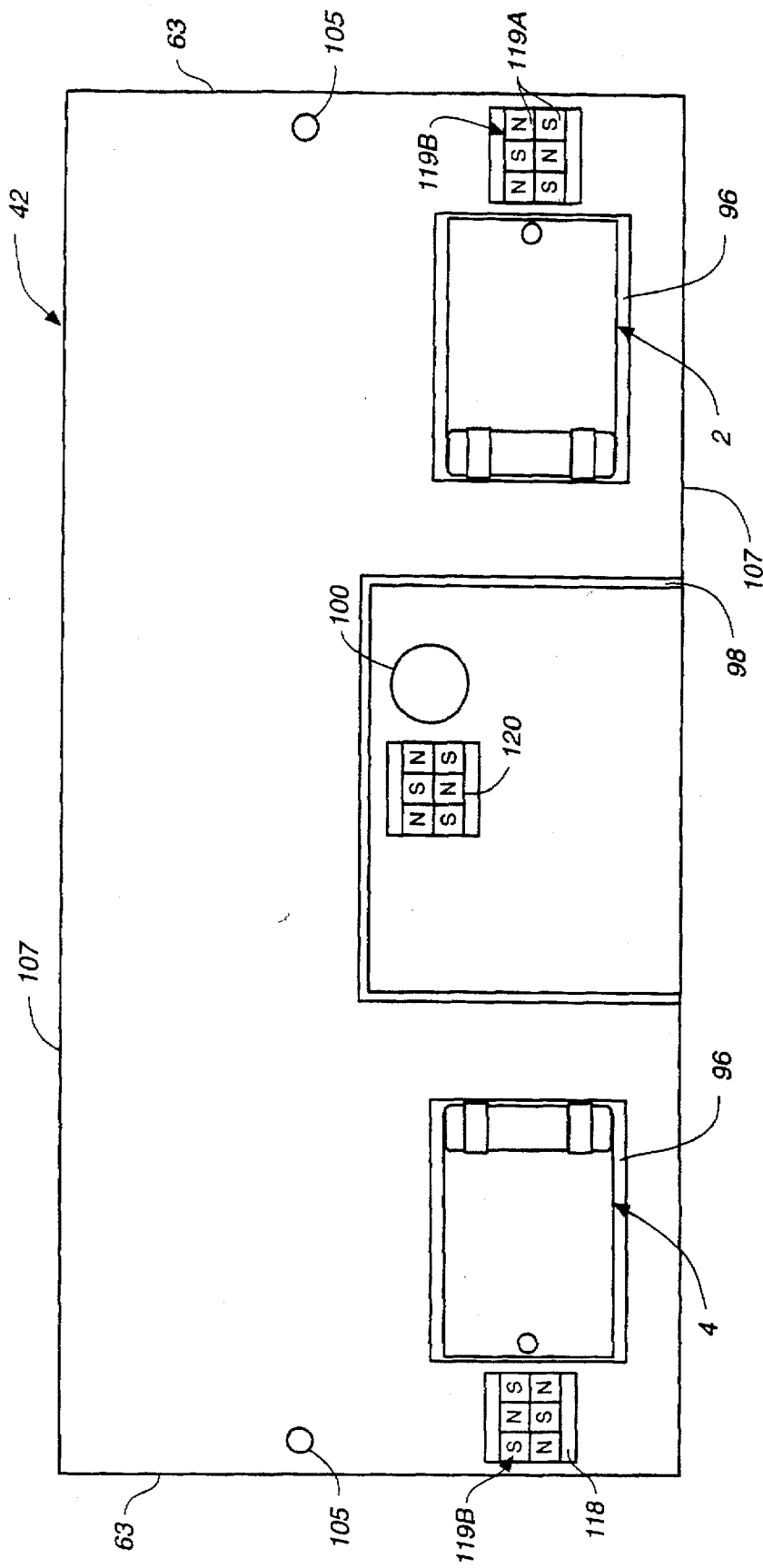
FIG._9

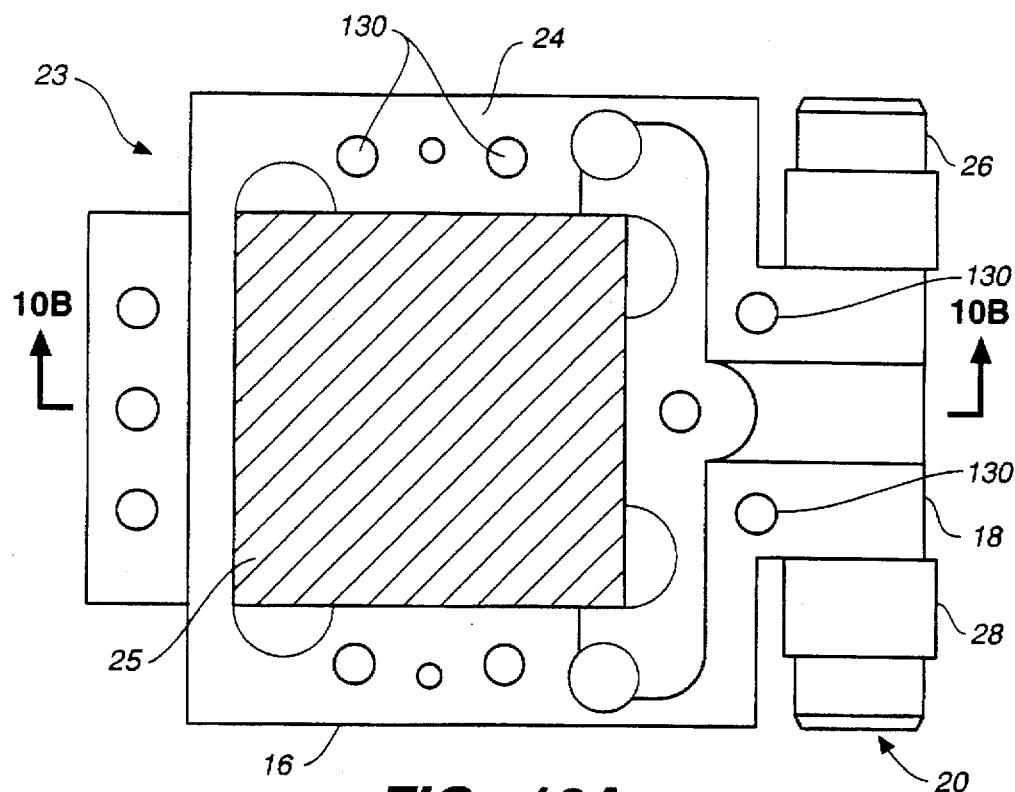
FIG._10A
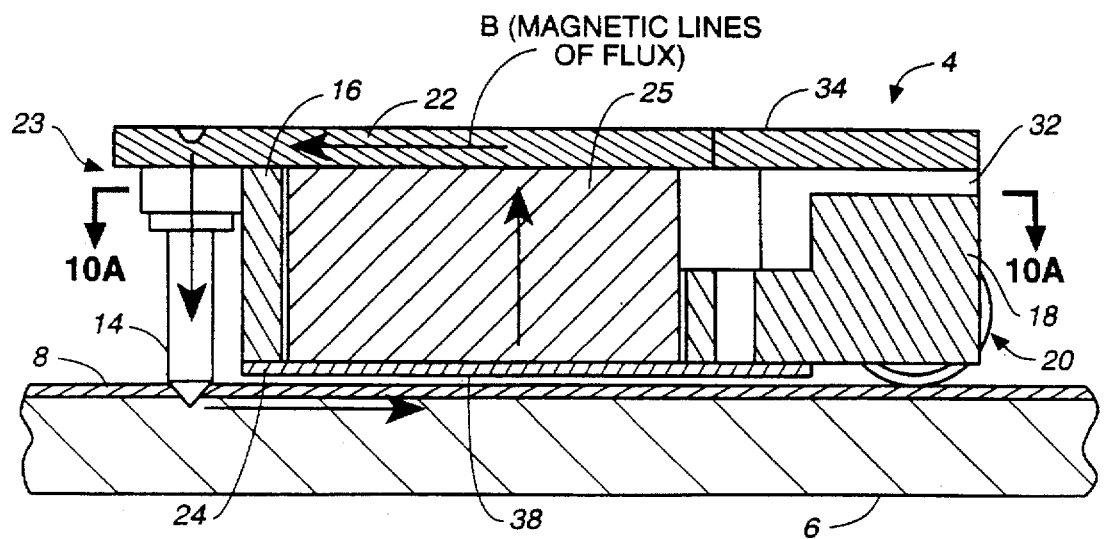
FIG._10B

ACOUSTIC STRAIN GAUGE AND ASSEMBLY AND METHOD FOR MEASURING STRAIN

This application is a Continuation-in-Part of application U.S. Ser. No. 08/707,922, filed Sep. 9, 1996 (Docket No. 53117).

FIELD OF THE INVENTION

The present invention relates to the field of devices and methods for measuring strain. More particularly, the invention relates to the measurement of strain on a given structure by determining the time of flight of acoustic waves in a material. The assignee of the present invention is also the assignee of an improved electromagnetic acoustic transducer which is disclosed and claimed in Mandracchia, U.S. Pat. No. 5,503,020, issued Apr. 2, 1996.

BACKGROUND OF THE INVENTION

Conventional resistance strain gauges measure the microstrain directly under the footprint of a small resistance gauge bonded to a prepared surface of a material of interest. As the material deforms, the resistance of the strain gauge changes, and a calculation of applied force or strain may be made of the measured material based on known characteristics. Because such measurements are confined to the immediate surface to which the strain gauge is bonded, the measurement is very discreet and does not necessarily represent the condition of the examined specimen in other areas of close proximity. The test technician in such a case, must choose the location of the strain gauge carefully, in reliance on the assumption that neighboring conditions are the same as those found in the detection area. What is needed is a strain measurement gauge which can be moved easily to measure greater areas of a material than those measured by conventional resistance strain gauges.

To prepare a structure for placement of a resistance-based strain gauge, the surface of the structure is usually prepared by removing paint and rust (sometimes by sandblasting), and by grinding and polishing the surface. The preparation for attaching such a gauge necessarily requires significant labor. In cases where the structure to be examined is a structural steel I-beam of, for example an older bridge, there is a likelihood that lead paint will have to be removed, an environmentally sensitive task. After laboriously preparing the surface of the structure to be analyzed, some kind of bonding medium is applied to the detection surface to affix or locate the resistance strain gauge to obtain good data. Dramatic reductions in test costs could be realized if data representing stress and strain could be obtained with limited surface preparation of the material to be analyzed.

A further limitation associated with utilizing conventional resistance strain gauges for measuring stress in bridges or other structures is that only measurements of surface stress or strain are detectable. Consequently, stresses or flaws underneath the immediate surface go unmeasured, and the technician evaluating the data must make critical assumptions about the overall integrity of the structure being examined based solely on the condition of its surface. What is needed then is a stable stress detection method which provides data at a greater depth than that produced by conventional resistance strain gauges.

To assist in solving these problems, acoustic instruments have been employed to measure stress and strain by measuring the time of flight of an acoustic wave through the material. Factors which can affect the measurement of a wave's time of flight ("TOF") include, but are not limited to: material properties such as texture, i.e., grain size and orientation; geometry of the specimen; and temperature.

One method of measuring stress or strain with acoustic instruments employs two or more orthogonal acoustic wave modes and/or measurement directions to cancel the aforementioned predominant unwanted effects. To date, either piezo-electric transducers or electromagnetic acoustic transducers ("EMATs"), have been employed in measuring TOF.

As set forth in assignee's aforementioned 5,503,020 patent, an EMAT generally comprises a conductor which is positioned within a static "biasing" magnetic field (B) near the surface of a conducting material. When an alternating current ($I_\omega$) is applied to the conductor, eddy currents ($J_\omega$) are induced within the surface layer of the conducting material. These induced eddy currents, in the presence of a biasing magnetic field, result in a Lorentz force which deflects the moving electrons in a direction defined by the vector product of $J_\omega \cdot B$. The electrons then collide with the ions in the lattice structure of the conducting material, ultimately generating acoustic energy in the form of an ultrasonic wave that propagates through the structure. The velocity (v) of the ultrasonic wave is determined by the scalar product of its wavelength ($\lambda$) and its frequency (f), i.e., $v = \lambda \cdot f$. The frequency of the ultrasonic wave is determined by that of the applied alternating current induced into the coil of the transmitting and receiving EMAT. Additionally, the orientation of both the biasing magnetic field and the induced eddy current determine the direction and mode characteristics of the propagating energy, and may be varied depending on how a technician wishes to examine a material, as well as the properties and configuration of the material itself.

EMATs have been fabricated with a variety of coil and magnet configurations to suit the requirements of particular applications. The teachings of U.S. Pat. Nos. 3,850,028, 4,048,847, 4,080,836, 4,092,868, 4,104,922, 4,127,035, 4,184,374, 4,218,924, 4,232,557, 4,248,092, 4,344,663 and 4,593,567, which are incorporated herein by reference, illustrate some of the configurations of EMATs, their application and their limitations.

In the case of continuous monitoring of stress using EMATs, care must be taken to compensate for any change in length under the EMATs and along the wave path due to deformation of the test piece. As the material under the EMAT is subjected to loading and unloading, it either elongates or compresses. As the material to be tested expands or contracts, it moves under the EMAT. This motion causes the EMAT to shift its position on the material. Exactly where the EMAT will be positioned on the material as it moves and after it moves is unpredictable; however, it is likely that the EMAT will shift position due to such moves. Under typical conditions, an EMAT can shift along the wave path, typically the longitudinal axis of the test material, or if the contact with the material is asymmetric, the EMAT may also rotate. Changes in position of the EMAT as small as one millionth of an inch will cause errors in acquired data.

It would be desirable to measure the applied stresses in a structure by measuring the relative times of flight of single acoustic wave forms with EMATs having a fixed footprint, i.e., each EMAT remains precisely positioned above the test surface regardless of any change in length in the test piece along the test wave path.

Many EMAT's currently on the market are constructed with a flat bottom which rests on the workpiece to be analyzed. During the aforementioned stress and strain which occurs in the workpiece, the amount of contact surface area comprising the bottom of a flat EMAT affects the movement of the EMAT on the workpiece. To date, no prior art teaches a method or EMAT device configuration for minimizing the contact area of an EMAT bottom, nor is there any other known method of minimizing friction between the EMAT contact area and the workpiece. Also, no prior art teaches a technique to readily anchor or fix the position of the EMATs relative to the surface of the workpiece.

SUMMARY OF THE INVENTION

Broadly stated, the present invention encompasses an improved acoustic strain gauge using one or more EMATs, typically one EMAT to transmit and one to receive acoustic waves, and a method of fixing the EMATs to a specimen or workpiece to be tested. The EMAT comprises a printed circuit board (PCB) and a source of magnetic flux for establishing a static magnetic field in the workpiece. The PCB, in turn, comprises a plurality of coil layers, an interconnect layer and a ground plane. The transmitting EMAT introduces energy into the specimen or workpiece at the instant a high speed counter, indexed to the zero crossing of the measured wave signal, begins operation. The acoustic energy traverses the distance from the transmitting EMAT to the receiving EMAT, where it is detected and converted into an electrical signal. The termination of the measurement event is indexed to an area of the detected wave such as its zero crossing, or other readily recognizable portion of the electrical signal of the detected wave. The time differential represents the TOF of the acoustic tone burst.

To measure applied stresses, the specimen is measured in an unstressed condition and then in a stressed condition. The change in TOF is calculated and stored. Typically, the change in TOF of a specimen under stress versus its unstressed condition is a function of: (1) the direction of the principal stresses relative to the measurement direction used; (2) specimen elongation, or strain; (3) velocity changes due to acoustoelasticity; and (4) temperature. However, as long as the combination of these effects is predictable and subject to limitations based on the structural material in question and its geometry, the TOF comparison can be relied on as a reliable source of information for measuring actual applied strain.

In particular, the improved acoustic strain gauge of the present invention comprises an EMAT body to house each of the EMATs having affixed to it a pin in general alignment with the body's longitudinal axis. Each EMAT body has an outer plane which is the bottom surface of the PCB in close proximity to the surface of the workpiece when the gauge is fixed into position. The pin extends a predetermined distance beyond the outer plane of the EMAT body. The pin has an upper end for striking and a lower end, which lower end is in contact with the workpiece directly thereunder. A holddown means is present either within the EMAT body or on the lower end to prevent the body from moving with respect to the workpiece. The EMAT body also has affixed to it a friction reducing means for engaging the workpiece and for supporting the body thereon. When the pin is struck, the pin indents the workpiece locating the outer plane of the EMAT body in substantially coplanar registry with the workpiece.

The holddown means can be a magnet within the EMAT body. The EMAT source for the magnetic flux is designed to have sufficient magnetic force to serve as the holddown means. Alternatively, the holddown means can comprise any suitable fastener or a layer of an epoxy spread between the lower end and the workpiece or other means of anchoring the pin into the non-ferrous metal workpiece, e.g., aluminum.

The gauge of the present invention prevents surface deformations occurring in the workpiece from affecting the registry of the EMAT body on the workpiece and minimizes unwanted frictional forces between the outer plane of the EMAT body and the workpiece and minimizes unpredictable movement of the EMAT relative to the workpiece. The present invention also provides a way to establish the EMAT in fixed registry with the workpiece to be analyzed.

Although the outer plane of the EMAT body may be altered geometrically to minimize the contact surface area and thus unwanted frictional influences, the gauge of the present invention is fabricated with a friction reducing means to allow deformation of the workpiece under the EMAT without compromising the registry between the two.

In one embodiment of the present invention, rails are provided as the friction reducing means on the outer plane, extending in the direction of the anticipated workpiece strain to minimize unwanted frictional forces.

In another embodiment of the present invention, low friction wheel assemblies or bearings provide the contact surface on the underside of the EMAT body to facilitate movement, while the pins affixed to the EMAT body maintain the registry between the EMAT transducer or receiver and the workpiece.

In the method of the present invention, the applied strain in the workpiece are measured by carrying out the following the steps:

(1) moving the pair of EMATs, positioned a fixed distance from each other, until the outer plane is in close proximity to the surface of the workpiece;

(2) striking the upper end of the pin to engage the lower end into the workpiece to fix the position of the body with respect to the workpiece;

(3) holding down the body with the holddown means so that the body remains motionless with respect to the workpiece;

(4) transmitting an acoustical wave traversed through the fixed distance via one of the EMATs and receiving the acoustic wave in the other EMAT; and (5) measuring the difference in TOF between the workpiece in the unstressed condition and stressed condition.

In still another embodiment of the present invention, an acoustic strain gauge assembly is provided in which a pair of the EMAT gauges are positioned on a workpiece to continually monitor applied strain by utilizing a mechanism operably connected to the EMATs and housed in a chassis held down on the workpiece by a holddown means in a similar manner to the EMAT holddown means. An actuating means raises or lowers the mechanism, locating the EMATs on the workpiece where they can be fixed into position by their pins. Such an actuating mechanism can be mechanical or electronic, simply serving to work the mechanism to raise or lower the EMATs onto the workpiece. The chassis also provides a structure for mounting a temperature sensor for correction data used in analyzing and processing the data generated by the EMATs. The chassis also provides support for one or more printed circuit boards (PCBs) and a computer interface port for transmitting data to a computer.

BRIEF DESCRIPTION OF THE DRAWINGS

Further features and advantages will become apparent from the following and more particular description of the preferred embodiments of the invention, as illustrated in the accompanying drawings, in which like reference characters generally refer to the same parts or elements throughout the views, and in which:

FIG. 1 is a isometric view of the basic gauge of the present invention of two separate EMAT bodies being located on the I-beam by striking a punch integral to each device with a hammer;

FIGS. 2A and 2B are the respective isometric views of the bottom and top of one of the EMAT bodies;

FIG. 2C is a cross-sectional view taken along line 2C—2C as shown in FIG. 3B;

FIG. 3A is a schematic side elevational view of FIG. 2 illustrating a fixed distance "L" between the EMATs according to the present invention;

FIG. 3B is an enlarged schematic side elevational view of one of the gauges as it would appear on a surface coated with paint;

FIG. 4 is an isometric view of the assembly of the present invention providing a unitary housing for the arrangement shown in FIG. 1 with a computer plug port;

FIGS. 5A and 5B are the respective side, partially cross-sectional views taken generally along line 5B—5B of FIG. 4 showing the units in the "up" and "down" positions;

FIGS. 6A and 6B are the respective side, partially cross-sectional views of FIGS. 5A and FIG. 5B taken along lines 6A—6A and 6B—6B, respectively;

FIG. 7 is a top plan view taken generally along line 7—7 in FIG. 6B;

FIG. 8 is a bottom plan view of the bottom of the assembly of the present invention as shown in FIG. 4;

FIG. 9 is a bottom plan view of the bottom of the assembly of the present invention showing the polarity of the array of holddown magnets for the chassis;

FIG. 10A is a top view of the EMAT within the EMAT body shown in FIG. 2B; and

FIG. 10B is a side view of the EMAT within the EMAT body in FIG. 2B.

DETAILED DESCRIPTION OF THE INVENTION

In a preferred embodiment of the gauge of the present invention, an extension of the EMAT body provides the housing for two wheel or bearing assemblies comprising low friction wheels or bearings operably mounted to the extension. The plate on the EMAT body, which also completes the magnetic circuit of the EMAT, extends beyond the body and has a conventional center punch as a positioning pin engaged therein which extends past the outer plane of the EMAT body. In the preferred embodiment, the pin has a hardened pointed lower end to increase its effectiveness in positioning the pin in the workpiece. When the pin is struck, its hardened lower pointed end engages the beam or other workpiece underneath, and establishes the outer plane of the EMAT in coplanar registry therewith.

It is anticipated that the pins or pointed positioners may be affixed to the EMAT by several means, for example: welding to the EMAT body or frame; being attached in a bushing which is sized to retain the positioner in position against the EMAT body or frame; retained in a housing with a latching means such that the pin is locked into position against the EMAT after having traveled a predetermined distance toward and into the workpiece. Suffice it to say a variety of methods may be employed to affix the pins or positioners to the EMAT to accomplish the purpose of indenting the workpiece and fixing the position of the EMAT on the workpiece.

In a preferred embodiment of the assembly of the present invention, the chassis is positioned on the workpiece and held into place by either a layer of an epoxy spread around a portion of the bottom of the chassis or an array of magnets when the workpiece is a ferrous metal, i.e., steel and/or other magnetizable metals. The holddown means help locate the chassis on a workpiece prior to lowering the EMATs into position. In such a configuration, a second set of positioning pins may be provided to affix the chassis to the workpiece as well as the EMATs. If magnets are used, it is critical to position them in such a manner to avoid any interference with the magnetic circuit of the EMATs.

In the preferred embodiment of the assembly, the chassis is also provided with an actuating handle and a mechanism (currently a plurality of links) which allows one or more EMATs to be lowered by a lifting post and lifting lug into position directly above a workpiece. Where two EMAT bodies are used, they are positioned a predetermined distance apart, and that distance is set by striking the positioning pins of each EMAT assembly. Preferably, the chassis and linkages are aluminum to minimize weight. An actuating handle operates the positioning mechanism, and the positioning pins for the EMAT bodies as well as the chassis itself are available through the top of the chassis. PCBs are also enclosed in the chassis to process information from the EMATs and a temperature sensor for compensating calculations are in communication with the PCBs. A computer interface port is provided in one end of the chassis for transmitting data to a computer for further analysis.

Referring now to the figures, FIG. 1 shows the position of transmitting and receiving EMAT gauges 2 and 4 on a metal I-beam 6. Typical of most structural ferrous metal I-beams used in structural applications outdoors, coating 8 of paint has been applied to beam 6 to prevent corrosion. A hammer 10 is shown in position to strike punch 12, thereby driving positioning pin 14 through paint coating 8 and into beam 6 as further illustrated in FIG. 3B.

In FIGS. 2A and 2B, the arrangement of either EMAT gauge 2 or 4 is shown in further detail. EMAT gauges 2 and 4 are comprised of an EMAT body 16 which has extended portion 18 to provide structure for a pair of bearing assemblies 20. Plate 22, which provides support for positioning pin 14, is constructed of magnetizable metal and serves to complete the magnetic circuit of EMAT 23 consisting of EMAT coil PCB 24, the bottom of which forms the outer plane of body 16 opposite that of plate 22, and magnet 25 shown in FIGS. 10A and 10B. The details of the construction of EMATs are further described in the assignee's 5,503,020 patent, the pertinent portions of which are incorporated by reference herein. Bearing assemblies 20 each comprise fastener 26 engaged in extended portion 18, securing bearing 28 thereto. Data transmission cable 30 passes through opening, channel or groove 32 (FIG. 10B) of extended portion 18 (FIG. 10B). Cover 34, typically of aluminum, is affixed to extended portion 18 protecting and securing data transmission cable 30.

As shown in FIG. 2B, a plurality of screws 36 respectively affix plate 22 to EMAT body 16 and cover 34 to extended portion 18. Cover 34 may be affixed to extended portion 18 in any other suitable way to accomplish the purpose of securing and protecting cable 30.

FIG. 2C shows a cross-section of extended portion 18 in which tapped hole 27 has suitable fastener 26, i.e., a shoulder screw or bolt, engaged therein to secure bearing 28.

FIG. 3A shows the positioning pins 14 of EMAT gauges 2 and 4 at a specific distance L from each other. As will be further described in FIG. 3B, positioning pins 14 locate EMAT gauges 2 and 4 in registry with beam 6, the bearing assemblies 20 providing a friction reducing means for allowing the surface of beam 6 to deform in compression or elongation, without changing the registry of either of the EMAT gauges 2 or 4.

FIG. 3B illustrates the position of EMAT 2 above a workpiece 10 after positioning pin 14 has been struck, penetrating paint layer 8 on beam 6. Bearing assembly 20 in extended portion 18, in combination with positioning pin 14, establishes outer plane 38 of EMAT gauges 2 and 4 in a substantially coplanar relationship with and at a precise distance from beam 6. In the embodiment shown in FIG. 3B, positioning pin 14 comprises a threaded commercial punch sized to extend the proper length from plate 22.

FIG. 4 shows EMAT gauge assembly 40 which was constructed to demonstrate the utility of the present invention. Assembly 40 comprised chassis 42, approximately 12" long and 4.5" wide and constructed of aluminum, operated by handle 44 which was used to reliably position EMAT gauges 2 and 4 above a workpiece. FIG. 4 shows the top striking end of two retractable punch extensions 46 and two chassis positioning pins 48, which were utilized to fix the position of both chassis 42 and the EMATs it housed to an underlying workpiece. Punch extensions 46 extended through a pair of first top holes 47 in top wall 43 of chassis 42, and chassis positioning pins 48 extended through a pair of second top holes 49 provided in top wall 43 of chassis 42. Handle 44 had two posts 50 extending downward therefrom. Posts 50 extended through slide 52, the upper portion of which formed grip 54. A pair of springs 56 mounted on posts 50 bias handle 44 from slide 52. Slide 52 had notch 58, which was engageable with latch 60 pivotally affixed to handle 44 to retain slide 52 proximate to handle 44. Slot 62 was provided in one end wall 63 of chassis 42 for locating a computer interface connector port 64 for transmitting data received by internal EMAT gauges 2 and 4. The action of slide 52 up and down posts 50 operated a linkage mechanism to position at least one EMAT gauge above a workpiece, as will now be described in detail.

FIG. 5A shows handle 44 and its two slide posts 50. At one end of handle 44, latch 60 was pivotally affixed to the handle by pin 66. Pre-loading latch 60 was spring 68, extending from small bore 70 in handle 44. Latch 60 is shown in engagement with notch 58 in slide 52. A pair of stepped bores 72 were provided in slide 52 forming a pair of shoulders 74. The pair of springs 56 bore against each shoulder 74, pre-loading handle 44 away from slide 52 as it travels along posts 50. Two L-shaped actuating links 78 were connected to slide 52 by a pair of pins 80. In this preferred embodiment, each actuating link 78 was L-shaped to allow positioning EMAT gauges 2 and 4 on each side of chassis 42's longitudinal axis. Lifting links 78 passed through a pair of slots 79 located a predetermined distance from the center of top wall 43 of chassis 42. A pair of Y-shaped lifting links 82 were joined to actuating links 78 by a pair of pins 84. The yoke ends of each lifting link 82 were connected by clevis pin 86 to clevis 88, which were each affixed to chassis 42. Each lifting link 82 provided a slotted bearing surface 90. EMAT gauges 2 and 4 were each provided with lifting post 92 extending from plate 22 and lifting lug 94. Lifting posts 92 passed through slotted bearing surfaces 90 such that when lifting links 82 were raised or lowered, each of the bearing surfaces 90 engaged lifting lugs 94, and similarly raised or lowered each of the EMAT gauges 2 and 4. The raising or lowering was accomplished by the raising or lowering of slide 52 along posts 50, moving actuating links 78 attached to lifting links 82, which in turn raised or lowered in pivotal rotation from devises 88.

Further shown in FIG. 5A are several access ports 96 and 98 located in bottom wall 99 of chassis 42. Access ports 96 were aligned with EMAT gauges 2 and 4 such that when in their lowered position, they were positioned directly on the workpiece below. Access port 98 were provided near the center of bottom wall 99 of chassis 42 for locating temperature sensor 100, whose function was to record changes in temperature of the workpiece directly below, which changes must be factored into data transmitted by the EMATs. Temperature sensor 100 was mounted within plastic plate 101 which serves to insulate sensor 100 from the thermal effects of bottom wall 99 and workpiece 6.

In FIG. 5B, EMAT gauges 2 and 4 had been lowered into position in access ports 96, guided by lifting links 82. The position of slide 52 is shown in a direction away from handle 44, having been released by disengaging latch 60 from notch 58. Temperature sensor 100 remained in position in center access port 98 in both FIGS. 5A and 5B.

The positions of retractable punch extensions 46 are also shown in FIGS. 5A and 5B. Punch extension 46 located above EMAT gauge 4 is shown in the retracted state. Punch extension 46 shown in alignment with EMAT gauge 2 was compressed by striker 102 until the bottom edge of extension 46 contacted the top of positioning pin 14. Striker 102 was pressed in engagement with pin 14 until a striking force was transmitted thereto. Once struck, pin 14 extended past the bottom of chassis 42 engaging beam 6 as previously shown in FIG. 3B. Punch extension 46 retracted back into its at rest position by the force of bias spring 104. Chassis positioning pins 48 (FIG. 4) were also struck, projecting each through chassis 42 at bottom holes 105, to fix the position of chassis 42 to beam 6 in addition to positioning pins 14 of EMAT gauges 2 and 4.

FIGS. 6A and 6B show sectional end views of chassis 42, particularly showing the action of slide 52. FIG. 6A shows slide 52 in its raised position where lifting lug 94 was engaged in bearing surface 90 of lifting link 82. FIG. 6A also shows the yoke configuration of lifting link 82. FIG. 6B shows EMAT gauge 2 in the lowered position, with positioning pin 14 engaged in I-beam 6.

FIG. 7 shows the relative positions of the internals of chassis 42 including EMAT gauges 2 and 4 in position in access ports 96. In this preferred embodiment, outer plane 38 of EMAT gauges 2 and 4 (FIG. 3B) was located substantially coplanar with beam 6 directly below, spaced in the neighborhood of 0.015" from beam 6. The dimension of 0.015" may vary according to the thickness of paint layer 8 on beam 6 (FIG. 3A). In some cases, variations in the thickness of paint layer 8 may exceed beyond 0.015" to approximately 0.030" or more. Accordingly, in such cases, outer plane 38 may be spaced up from beam 6. The farther away from beam 6 outer plane 38 is, the more sensitive the EMATs must be. It is desirable to have outer plane 38 as close to beam 6 as possible without touching the beam. In this way, unwanted frictional forces do not skew outer plane 38, and the only contact points between EMAT gauges 2 and 4 and beam 6 are bearing assemblies 20 and positioning pin 14. PCB 106 is shown in FIG. 7 in communication with data communication cables 30 from EMAT gauges 2 and 4, as are also shown with communication cables 108 from temperature sensor 100. Again, the yoke-like configuration of lifting link 82 is shown, as well as clevis pin 86, which pivotally affixed the lifting link to clevis 88. Bottom holes 105 in bottom wall 99 of chassis 42 are shown a predetermined distance from both side walls 107 of chassis 42. When chassis positioning pins 48 (FIG. 4) were struck extending through bottom holes 105, a stable footprint was established for fixing chassis 42 to beam 6 directly below.

FIG. 8 further shows the layout of bottom wall 99 of chassis 42. The relative positions of access ports 96 and 98 are seen as well as bottom holes 105 and magnet access ports 118. The precise number and location of magnet access ports 118 containing a predetermined array of magnets 119A for initially positioning and maintaining chassis 42 on a beam depend on the size and weight of chassis 42. In the embodiment shown in FIG. 8, an array of six magnets 119A were provided in each of the two magnet ports 118 in bottom wall 99 and were used to initially secure chassis 42 to beam 6 prior to positioning EMAT gauges 2 and 4 and to securely anchor chassis 42 during testing. Each magnet 119A was 0.25 by 0.25 inch square by 0.5 inch high. Each of the array of six grade 35 magnets 119A were embedded or potted within port 118 in holddown package 119B of epoxy. Each holddown package 119B of six magnets 119A supported about five pounds or about 14 pounds per square inch of magnetic force. Magnets 119A were arranged in holddown package 119A with alternate polarities so that the resulting magnetic field did not cause any interference with magnetic lines of flux B generated by each of magnets 25 of EMATs 23 (FIG. 10B). Ports 118 in bottom wall 99 were positioned so that holddown packages 119B were axially aligned with the EMAT acoustic path and placed behind EMAT 23 for axial symmetry. Each of ports 118 was ½ inch wide and ¾ inch long and was centered in bottom wall 99 along the center line of the EMAT acoustic path so that the outer edge of port 118 was about ½ inch from end wall 63 and 1½ inches from the outer wall of magnet 25. Bottom wall 99 was covered with electrically insulating Kapton film by means of an adhesive to prevent electrical continuity between chassis 42 and workpiece 6. The pair of EMAT gauges 2 and 4 were spaced so that positioning pins 14 were about 9 inches apart on bottom wall 99. The array of magnets 119A were arranged with alternate north and south polarities as shown in FIG. 9.

In FIGS. 10A and 10B, EMAT 23 is shown comprising EMAT coil PCB 24, magnet 25, extended portion 18 to which bearing assembly 20 was affixed as described above. EMAT coil PCB 24 consisted of the EMAT coil embedded in FR-4 flame-retardant epoxy-woven glass board in accordance with the American NEMA specification. Tapped holes 130 are located around the periphery of PCB 24 for fasteners 36 shown in FIG. 2B. The magnetic field or lines of flux B are depicted by directional arrows in FIG. 10B.

EXAMPLE

A first EMAT gauge assembly 40 was set up on an area at a known load point of a steel bridge and a reading was taken at that point in an unstressed condition during 6 to 10 minutes. Similarly, a second assembly 40 was set up in another such area during the same amount of time. The set up time for the assembly of this invention is compared with that required for the prior art resistance-based strain gauges. To prepare the surface of a bridge and to set up the prior art gauge before a first reading can be made requires an order of magnitude more time, i.e., approximately one hour.

Assembly 40 shown in FIG. 8 was found to rotate off the workpiece due to the movement of the cable connecting to port 64. As a result of such movement, erroneous readings occurred. These erroneous readings were eliminated by adding third magnet port 120 in bottom 99 containing package 119B of six magnets 119A having alternate polarities as shown in FIG. 9. Port 120 was centered between end walls 63 and positioned to avoid interference with the magnetic lines of flux B of EMATs 23. Specifically, the bottom edge of package 119B was ⅞ inch from the bottom edge of package 119B in port 118 and approximately 1⅜ inches from the centerline of the acoustic path of EMATs 23. By the addition of the third holddown package 120, no further erroneous readings occurred as a result of cable movement. The proper ratio is one holddown package for each approximately 2½ pounds of EMAT assembly used in testing.

While the invention has been described in connection with what is presently considered the most practical and preferred embodiment(s), it is to be understood that the invention is not limited to the disclosed embodiment(s) but, on the contrary is intended to cover various modifications and equivalent arrangements included within the scope of the appended claims.

What is claimed is:

1. An improved acoustic strain gauge for transmitting and receiving acoustic waves through a workpiece comprising:

a pair of Electromagnetic Acoustic Transducers ("EMATs") for respectively transmitting and receiving acoustic waves through said workpiece and for determining the applied strain in the workpiece by measuring the change in time of flight between the workpiece in the stressed and unstressed condition for determining applied strain;

a body for housing each of said EMATs, each of said bodies having an outer plane and a longitudinal axis;

a pin fixed relative to each of said bodies' longitudinal axis, said pin extending a first predetermined distance beyond said outer plane for engaging the workpiece to fix the position of said outer plane with respect thereto and to maintain the coplanar registry between each EMAT and the workpiece at a second predetermined distance, said pin having an upper end for striking and a lower end for engaging the workpiece;

holddown means for preventing said body from moving with respect to the workpiece; and a friction reducing means affixed to each of said bodies for engaging the workpiece and supporting said EMAT thereon such that when said pin is struck thereby indenting the workpiece and locating said outer plane in substantially coplanar registry therewith, surface deformations occurring in the workpiece have negligible effect on the position of the body thereon and for allowing deformation of the workpiece under each EMAT without compromising the registry between the pair of EMAT's.

2. The gauge as described in claim 1 wherein said friction reducing means comprises a bearing assembly.

3. The gauge as described in claim 1 wherein said friction reducing means comprises at least one low friction bearing affixed to said body.

4. The gauge as described in claim 1 wherein the distance between said outer plane and the workpiece is approximately 0.015".

5. The gauge as described in claim 1 wherein said holddown means comprises a fastener between the lower end of said pin and the workpiece.

6. The gauge as described in claim 1 wherein said holddown means comprises a layer of an epoxy spread between the lower end of said pin and the workpiece.

7. The gauge as described in claim 1 wherein said workpiece comprises magnetizable metal and said holddown means comprises a magnet within said body having sufficient magnetic force to prevent movement of said EMATs with respect to the workpiece and positioned in said body.

8. The gauge as described in claim 1 wherein the workpiece comprises magnetizable metal and said EMATs comprise a PCB and a source of magnetic flux for establishing a static magnetic field in the workpiece and said magnetic flux source having sufficient magnetic force to serve as said holddown means.

9. An improved acoustic strain gauge for transmitting and receiving acoustic waves through a steel workpiece comprising:
    a pair of EMATs for respectively transmitting and receiving acoustic waves through said workpiece and for determining the applied strain in the workpiece by measuring the change in time of flight between the workpiece in the stressed and unstressed condition for determining applied strain, each of said EMATs having a PCB and a source of magnetic flux for establishing a static magnetic field in the workpiece and said magnetic flux source having sufficient magnetic force to prevent movement of said EMATs with respect to the workpiece;
    a body for housing each of said EMATs having an outer plane and a data transmission cable, said body having an extended portion on one end;
    said extended portion having a top surface, a bottom surface, a rear surface, and two side surfaces, said top surface forming an opening for guiding said transmission cable;
    a cover affixed to said extended portion covering said top surface;
    a plate affixed to and extending beyond each of said EMATs, said plate having a hole therethrough, said hole being positioned in alignment with the longitudinal axis of said EMATs;
    a pair of low friction bearings operably connected to said extended portion such that when at rest, said outer plane is substantially parallel with respect to the workpiece; and
    a positioning pin in said plate's hole and extending a first predetermined distance beyond said outer plane, said pin having an upper end for striking and a hardened pointed lower end, such that when said EMATs are placed upon the workpiece, striking said pin drives said pin into the workpiece thereby retaining said EMATs in coplanar registration therewith at a second predetermined distance from the workpiece.

10. The gauge of claim 9 wherein said outer plane is located approximately 0.015" from the workpiece after striking said positioning pin.

11. The gauge of claim 9 wherein each of the side surfaces of said extended portion has a tapped hole and wherein a fastener passes through the center of each low friction bearing and engages the tapped hole to retain each of said bearings proximate to said extended portion.

12. An acoustic strain gauge assembly for continually monitoring stress in a workpiece comprising:
    a chassis;
    first holddown means for preventing said chassis from moving with respect to the workpiece;
    a pair of EMATs for respectively transmitting and receiving acoustic waves through said workpiece and for determining the applied strain in the workpiece by measuring the change in time of flight between the workpiece in the stressed and unstressed condition for determining applied strain, each of said EMATs having a PCB and a source of magnetic flux for establishing a static magnetic field in the workpiece;
    an EMAT body for housing each of said EMATs having an outer plane and a longitudinal axis;
    a pin fixed relative to each of said EMAT bodies aligned with said body's longitudinal axis, said pin extending a first predetermined distance beyond said body, said pin having an upper end for striking and a lower end for engaging the workpiece to fix the position of said EMAT body with respect thereto and to maintain coplanar registry between each EMAT and the workpiece at a second predetermined distance;
    second holddown means for preventing each of said EMAT bodies from moving with respect to the workpiece;
    friction reducing means affixed to each of said EMAT bodies for engaging the workpiece and supporting said body thereon and for allowing deformation of the workpiece under each EMAT without compromising the registry between the pair of EMATs;
    a mechanism affixed in said chassis, said mechanism operably connected to each of said EMAT bodies such that said mechanism raises and lowers said EMATs onto the workpiece; and
    means for actuating said mechanism.

13. The assembly as described in claim 12 wherein said mechanism comprises a series of links connected to said chassis and said actuating mechanism.

14. The assembly as described in claim 12 wherein said actuating means comprises a handle in combination with a slide, said slide operably connected with said mechanism.

15. The assembly as described in claim 12 wherein said actuating means is electronically operated.

16. The assembly as described in claim 12 wherein said mechanism is electronically operated.

17. The assembly as described in claim 12 wherein said workpiece comprises a non-ferrous material and said first holddown means comprises a layer of an epoxy spread between the lower end of said pin and the workpiece.

18. The assembly as described in claim 12 wherein said workpiece comprises magnetizable metal and said first holddown means comprises at least one array of magnets having sufficient magnetic force to prevent movement of said chassis without interfering with a static magnetic field established by said EMAT.

19. The assembly as described in claim 12 wherein said first holddown means comprises at least two arrays of magnets positioned on said chassis to prevent interference with a static magnetic field established by said EMAT.

20. The assembly as described in claim 12 wherein said second holddown means comprises a fastener between the lower end of said pin and the workpiece.

21. The assembly as described in claim 12 wherein said second holddown means comprises a layer of an epoxy spread between the lower end of said pin and the workpiece.

22. The assembly as described in claim 12 wherein the workpiece comprises magnetizable metal and said source of magnetic flux for establishing a static magnetic field in the workpiece has sufficient magnetic force to serve as said second holddown means.

23. An acoustic strain gauge assembly for continually monitoring stress in a ferrous workpiece comprising:

a box-like chassis, said chassis having a top wall, a bottom wall, two end walls and two side walls, said top wall having two slots spaced at a predetermined distance from the center of said chassis, said top wall having two first top holes proximate to the longitudinal axis of said chassis and said end walls, said top wall having two second top holes parallel to said longitudinal axis and located a predetermined distance from said end walls, said bottom wall having two access ports parallel to said longitudinal axis and positioned on either side of a third access port, said bottom wall having two bottom holes directly below and in registry with said top wall's two first top holes, one of said end walls forming a slot for a PC interface connector port, said bottom wall having at least two ports proximate to said end walls;

an array of magnets affixed to said bottom wall and positioned within each of said ports having sufficient magnetic force to prevent said chassis from movement under an applied strain on the workpiece;

a pair of positioning pins extending through said first top holes in said top wall and said corresponding bottom holes in said bottom wall, said first positioning pins having a top end for striking and a bottom pointed end, said first positioning pins rigidly affixed to said chassis;

a handle with two downward projecting posts;

a slide of generally rectangular shape and forming a grip, said slide having a pair of stepped bores each forming a shoulder, said slide having a notch on one end;

said handle and said posts passing through said slide, said posts affixed to said top wall of said chassis;

a pair of first springs located in said stepped bores and bearing against said shoulders and said handle pre-loading said handle away from said slide;

a latch, pivotally affixed to said handle and biased toward said notch by a second spring, said latch engageable with said notch for retaining said slide proximate to said handle;

a pair of L-shaped actuating links passing through said slots;

a first pair of link pins rotatably affixing said actuating links to said slide;

a pair of Y-shaped lifting links having a singular end and two yoke ends opposite said singular end, each of said lifting links having a slotted bearing surface proximate to said yoke ends;

a pair of devises each affixed to an inside of said end walls at a predetermined distance from said bottom wall;

a pair of clevis pins, said clevis pins passing through said devises and said yoke ends of said lifting links pivotally affixing said Y-shaped lifting links to said devises;

a second pair of link pins passing through said single ends of said lifting links and said second holes in said actuating links pivotally affixing said lifting links to said actuating links;

at least a first PCB affixed to said bottom wall of said chassis;

a cable connector port affixed in said slot in said end wall, said connector port in communication with said first PCB;

a temperature sensor affixed in said third access port, said temperature sensor having a cable in communication with said first PCB;

a pair of gauges for transmitting and receiving acoustic waves through the workpiece comprising:

a pair of EMATs for respectively transmitting and receiving acoustic waves through said workpiece and for determining the applied strain in the workpiece by measuring the change in time of flight between the workpiece in the stressed and unstressed condition for determining applied strain, each of said EMATs having a second PCB and a source of magnetic flux for establishing a static magnetic field in the workpiece and said magnetic flux source having sufficient magnetic force to prevent movement of said EMATs with respect to the workpiece;

an EMAT body having an outer plane for each of said EMATs and a longitudinal axis;

a pin aligned with each of said bodies' longitudinal axis, said pin having an upper end for striking and a hardened pointed end for engaging the workpiece;

a friction reducing means affixed to each of said EMAT bodies for engaging the workpiece and supporting said body thereon such that when said pin is struck thereby indenting the workpiece and locating said outer plane in substantially coplanar registry therewith, surface deformations occurring in the workpiece have negligible effect on the position of the body thereon;

a lifting post for each of said EMAT bodies, each of said lifting posts passing through said slotted bearing surfaces in said lifting links, said cables in communication with said first and second PCBs positioned a predetermined distance above said access ports;

a pair of retractable punch extensions extending vertically downward from said second top holes in said top wall and in engageable alignment with said pins in said gauges; and each of said lifting posts having attached thereto a lifting lug, such that when said grip is squeezed, drawing said slide toward said handle, said actuating links move said lifting links upward, engaging said lifting lugs in said slotted bearing surfaces thereby drawing said EMAT away from said access ports, and conversely, when said latch is disengaged from said notch allowing said spring to pre-load said slide away from said handle, said actuating links move said lifting links downward, thereby lowering said EMAT bodies by said lifting lugs until said second PCBs are proximate to said access ports and so that when external force is applied to said positioning pins, said chassis is located in registry with the workpiece, and when external force is applied to said punch pin extensions, said pins of said gauges locate said second PCBs in registry with the workpiece.

24. The assembly as described in claim 23 wherein said friction reducing means comprises a bearing assembly.

25. The assembly as described in claim 23 wherein said friction reducing means comprises at least one low friction bearing affixed to said body.

26. A method for positioning a pair of EMATs for transmitting and receiving acoustic waves through a workpiece and measuring applied strain in the workpiece comprising the steps of:

moving a pair of EMATs positioned a fixed distance from each other, each of said EMATs being mounted in a body having an outer plane, until said outer plane is in close proximity to the surface of the workpiece, having a pin aligned with said body's longitudinal axis, said pin having an upper end for striking and a lower end for engaging the workpiece, and having a friction reducing means affixed to the body for engaging the workpiece and supporting said body thereon such that when said pin is struck thereby indenting the workpiece and locating said outer plane in substantially coplanar registry therewith at a predetermined distance from the workpiece, surface deformations occurring in the workpiece have negligible effect on the position of the body thereon and allow deformation of the workpiece under each EMAT without compromising the registry between the pair of EMATs;

preventing said body from moving with respect to the workpiece with a holddown means;

striking the upper end of said pin to engage the lower end into the workpiece to fix the position of said body with respect to the workpiece;

transmitting an acoustical wave transversed through the fixed distance via one of the EMATs and receiving the acoustic wave in the other EMAT; and measuring the difference in TOF between the workpiece in the unstressed condition and stressed condition and determining the applied strain on the workpiece.

27. The method of claim 26 wherein the temperature of the workpiece is monitored and factored into the measurement of the difference in TOF.

28. The method of claim 27 wherein the temperature of the workpiece is monitored by means of a temperature sensor within a plastic plate to insulate the sensor from thermal effects of said body.

29. The method of claim 26 wherein the distance between said outer plane and the workpiece is approximately 0.015".

30. The method of claim 26 wherein said holddown means comprises a fastener between the lower end and the workpiece.

31. The method of claim 26 wherein said holddown means comprises a layer of an epoxy spread between the lower end and the workpiece.

32. The method of claim 26 wherein the workpiece comprises magnetizable metal and said EMAT comprises a PCB and a source of magnetic flux for establishing a static magnetic field in the workpiece and having sufficient magnetic force to prevent movement of said EMAT with respect to the magnetizable metal workpiece.

* * * * *

UNITED STATES PATENT AND TRADEMARK OFFICE
CERTIFICATE OF CORRECTION

PATENT NO. : 5,750,900
DATED : May 12, 1998
INVENTOR(S) : Hugentobler, et al.

It is certified that error appears in the above-indentified patent and that said Letters Patent is hereby corrected as shown below:

Column 8, line 9, delete "were" and insert therefor --was--.

Column 13, line 51, delete "devises" and insert therefor --clevises--.

Column 14, line 53, delete "l east" and insert therefor --least--.

Column 15, line 4 after first occurrence of "workpiece" insert --to said outer plane--.

Signed and Sealed this

Twelfth Day of January, 1999

Attest:

Attesting Officer

*Acting Commissioner of Patents and Trademarks*